US012262936B2

(12) United States Patent
Tonn et al.

(10) Patent No.: US 12,262,936 B2
(45) Date of Patent: *Apr. 1, 2025

(54) SYSTEMS AND METHODS FOR CONTROLLED ELECTROSURGICAL COAGULATION

(71) Applicant: Covidien LP, Mansfield, MA (US)

(72) Inventors: Donald L. Tonn, Superior, CO (US); James E. Dunning, Boulder, CO (US); William D. Faulkner, Boulder, CO (US); Jennifer R. McHenry, Denver, CO (US); Devon E. Scott-Drechsel, Superior, CO (US); Eric M. Westra, Hudsonville, CO (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/232,469

(22) Filed: Aug. 10, 2023

(65) Prior Publication Data
US 2023/0380882 A1 Nov. 30, 2023

Related U.S. Application Data

(63) Continuation of application No. 16/122,857, filed on Sep. 5, 2018, now Pat. No. 11,744,631.
(Continued)

(51) Int. Cl.
A61B 18/12 (2006.01)
A61B 18/00 (2006.01)
A61B 18/14 (2006.01)

(52) U.S. Cl.
CPC ...... A61B 18/1206 (2013.01); A61B 18/1233 (2013.01); A61B 18/1442 (2013.01);
(Continued)

(58) Field of Classification Search
CPC ............ A61B 18/1206; A61B 18/1445; A61B 2018/00607
See application file for complete search history.

(56) References Cited

U.S. PATENT DOCUMENTS 5,472,443 A 12/1995 Cordis et al.
6,080,149 A 6/2000 Huang et al.
(Continued)

FOREIGN PATENT DOCUMENTS

DE 179607 C 11/1906
DE 390937 C 3/1924
(Continued)

OTHER PUBLICATIONS

U.S. Appl. No. 18/232,469, is a Continuation of U.S. Appl. No. 16/122,857, filed Sep. 5, 2018, Patented, U.S. Pat. No. 11,744,631.
(Continued)

Primary Examiner — Daniel W Fowler
Assistant Examiner — Annie L Shoulders

(57) ABSTRACT

The present disclosure includes an electrosurgical generator that controls treatment energy to be provided in a coagulation mode, where the treatment energy has an adjustable voltage ramp rate which can be set to a ramp rate in a range of voltage ramp rates. The generator receives signals from an instrument over time relating to load impedance. When the load impedance is above a threshold, the generator sets the adjustable voltage ramp rate to a ramp rate in the range of voltage ramp rates, and decreases, at the adjustable voltage ramp rate, a voltage of the treatment energy. When the load impedance is below the threshold, the generator sets the adjustable voltage ramp rate to a ramp rate in the range of voltage ramp rates, and increases, at the adjustable voltage ramp rate, the voltage of the treatment energy.

20 Claims, 4 Drawing Sheets

Related U.S. Application Data

(60) Provisional application No. 62/562,110, filed on Sep. 22, 2017, provisional application No. 62/562,012, filed on Sep. 22, 2017, provisional application No. 62/562,078, filed on Sep. 22, 2017.

(52) U.S. Cl.
CPC ............. *A61B 18/1445* (2013.01); *A61B 2018/00589* (2013.01); *A61B 2018/00595* (2013.01); *A61B 2018/00601* (2013.01); *A61B 2018/00607* (2013.01); *A61B 2018/0063* (2013.01); *A61B 2018/00642* (2013.01); *A61B 2018/00666* (2013.01); *A61B 2018/00702* (2013.01); *A61B 2018/00767* (2013.01); *A61B 2018/00827* (2013.01); *A61B 2018/00875* (2013.01); *A61B 2018/1253* (2013.01); *A61B 2018/126* (2013.01); *A61B 2018/1266* (2013.01); *A61B 2018/1462* (2013.01)

(56) References Cited

U.S. PATENT DOCUMENTS

| | | | |
|---|---|---|---|
| 6,468,270 B1 | 10/2002 | Hovda et al. | |
| 6,837,888 B2 | 1/2005 | Ciarrocca et al. | |
| 6,942,660 B2 | 9/2005 | Pantera et al. | |
| 6,974,453 B2 | 12/2005 | Woloszko et al. | |
| 7,070,596 B1 | 7/2006 | Woloszko et al. | |
| D574,323 S | 8/2008 | Waaler | |
| 9,270,202 B2 | 2/2016 | Johnson et al. | |
| 9,283,028 B2 | 3/2016 | Johnson | |
| 9,737,355 B2 | 8/2017 | Yates et al. | |
| 11,744,631 B2 * | 9/2023 | Tonn | A61B 18/1442 606/41 |
| 2002/0029036 A1 | 3/2002 | Goble et al. | |
| 2002/0165531 A1 | 11/2002 | Goble | |
| 2003/0028186 A1 | 2/2003 | Kreindel | |
| 2004/0167508 A1 | 8/2004 | Wham et al. | |
| 2005/0203504 A1 | 9/2005 | Wham et al. | |
| 2006/0217707 A1 | 9/2006 | Daniel et al. | |
| 2007/0173811 A1 | 7/2007 | Couture et al. | |
| 2007/0265616 A1 | 11/2007 | Couture et al. | |
| 2008/0221565 A1 | 9/2008 | Eder et al. | |
| 2008/0287944 A1 | 11/2008 | Pearson et al. | |
| 2009/0240244 A1 | 9/2009 | Malis et al. | |
| 2011/0028963 A1 | 2/2011 | Gilbert | |
| 2011/0037484 A1 | 2/2011 | Gilbert | |
| 2011/0038056 A1 | 2/2011 | Nakamura | |
| 2011/0208183 A1 | 8/2011 | Stockert | |
| 2012/0078139 A1 | 3/2012 | Aldridge et al. | |
| 2012/0179154 A1 | 7/2012 | Goldberg et al. | |
| 2013/0296908 A1 | 11/2013 | Schulte | |
| 2014/0018668 A1 | 1/2014 | Zheng et al. | |
| 2014/0025061 A1 | 1/2014 | Benamou | |
| 2014/0100559 A1 | 4/2014 | Wham et al. | |
| 2014/0232463 A1 | 8/2014 | Gilbert | |
| 2014/0243815 A1 | 8/2014 | Kerr | |
| 2014/0253140 A1 | 9/2014 | Gilbert | |
| 2014/0257270 A1 | 9/2014 | Behnke | |
| 2014/0258800 A1 | 9/2014 | Gilbert | |
| 2014/0276659 A1 | 9/2014 | Juergens et al. | |
| 2014/0276750 A1 | 9/2014 | Gilbert | |
| 2014/0276753 A1 | 9/2014 | Wham et al. | |
| 2014/0276754 A1 | 9/2014 | Gilbert et al. | |
| 2014/0358138 A1 | 12/2014 | Mattmiller et al. | |
| 2014/0376269 A1 | 12/2014 | Johnson et al. | |
| 2015/0025521 A1 | 1/2015 | Friedrichs et al. | |
| 2015/0025523 A1 | 1/2015 | Friedrichs et al. | |
| 2015/0032096 A1 | 1/2015 | Johnson | |
| 2015/0032098 A1 | 1/2015 | Larson et al. | |
| 2015/0032099 A1 | 1/2015 | Larson et al. | |
| 2015/0032100 A1 | 1/2015 | Coulson et al. | |
| 2015/0088116 A1 | 3/2015 | Wham | |
| 2015/0088117 A1 | 3/2015 | Gilbert et al. | |
| 2015/0088118 A1 | 3/2015 | Gilbert et al. | |
| 2015/0088124 A1 | 3/2015 | Wham | |
| 2015/0088125 A1 | 3/2015 | Wham | |
| 2015/0119871 A1 | 4/2015 | Johnson et al. | |
| 2015/0272657 A1 | 10/2015 | Yates | |
| 2015/0328474 A1 | 11/2015 | Flyash et al. | |
| 2016/0066978 A1 | 3/2016 | Keller et al. | |
| 2016/0175028 A1 | 6/2016 | Trees et al. | |
| 2016/0270841 A1 | 9/2016 | Strobl et al. | |
| 2016/0374746 A1 | 12/2016 | Takami et al. | |
| 2017/0000554 A1 | 1/2017 | Yates et al. | |
| 2017/0196621 A1 | 7/2017 | Wilson et al. | |
| 2021/0204996 A1 | 7/2021 | Ko et al. | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102008058737 A1 | 4/2010 |
| EP | 0246350 A1 | 11/1987 |
| EP | 0267403 A2 | 5/1988 |
| EP | 0296777 A2 | 12/1988 |
| EP | 0310431 A2 | 4/1989 |
| EP | 0325456 A2 | 7/1989 |
| EP | 0336742 A2 | 10/1989 |
| EP | 0390937 A1 | 10/1990 |
| EP | 0556705 A1 | 8/1993 |
| EP | 0608609 A2 | 8/1994 |
| EP | 0836868 A2 | 4/1998 |
| EP | 0880220 A2 | 11/1998 |
| EP | 0882955 A1 | 12/1998 |
| EP | 1051948 A2 | 11/2000 |
| EP | 1366724 A1 | 12/2003 |
| EP | 1776929 A1 | 4/2007 |
| EP | 2111812 A2 | 10/2009 |
| EP | 2649956 A1 | 10/2013 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |
| JP | 63005876 | 1/1988 |
| JP | 2002065690 A | 3/2002 |
| JP | 2005185657 A | 7/2005 |
| SU | 166452 | 11/1964 |
| SU | 727201 A2 | 4/1980 |
| WO | 0211634 | 2/2002 |
| WO | 0245589 | 6/2002 |
| WO | 03090635 A1 | 11/2003 |
| WO | 2006050888 A1 | 5/2006 |

(56) References Cited

FOREIGN PATENT DOCUMENTS

| WO | 2008053532 A1 | 5/2008 |
| WO | 2008071914 A2 | 6/2008 |

OTHER PUBLICATIONS

U.S. Appl. No. 16/122,857, Claims priority from U.S. Appl. No. 62/562,110, filed Sep. 22, 2017, Expired.
U.S. Appl. No. 16/122,857, Claims priority from U.S. Appl. No. 65/562,012, filed Sep. 22, 2017, Expired.
U.S. Appl. No. 16/122,857, Claims priority from U.S. Appl. No. 62/562,078, filed Sep. 22, 2017, Expired.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP", Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf- >, pp. 6, 11, 73.
Ogden, "Goertzel Alternative to the Fourier Transform": Jun. 1993 pp. 485-487 Electronics World; Reed Business Publishing, Sutton, Surrey, BG, vol. 99, No. 9, 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al.. "The Measurement of Physiologic Events by Electrical Impedence" Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994), pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B. V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
Extended European Search Report corresponding to counterpart Patent Application EP 18195885.1 dated Feb. 25, 2019.
Japanese Office Action dated Jul. 26, 2019 corresponding to counterpart Patent Application JP 2018-177157.

* cited by examiner

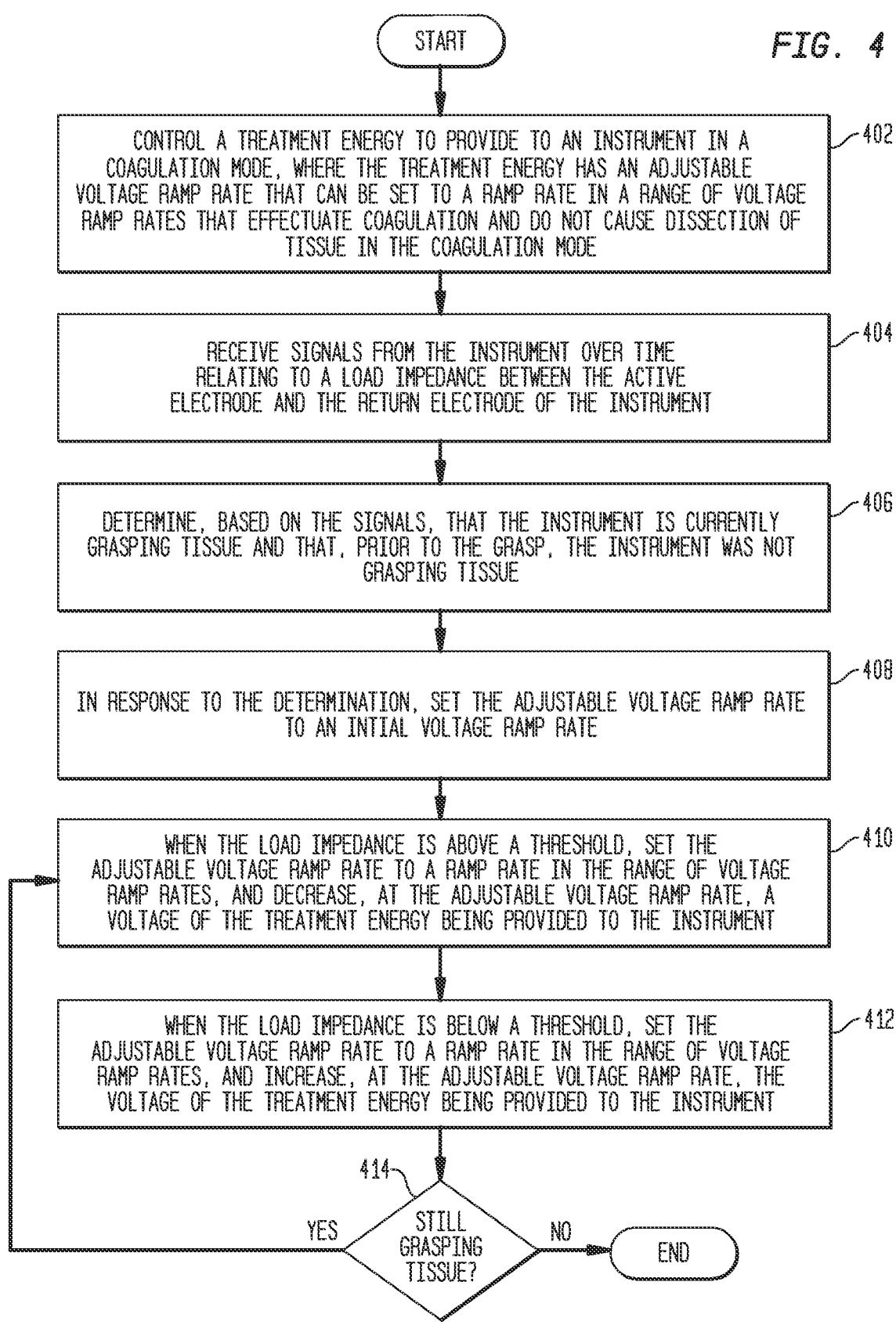

SYSTEMS AND METHODS FOR CONTROLLED ELECTROSURGICAL COAGULATION

CROSS-REFERENCE TO RELATED APPLICATIONS

This application is a continuation of U.S. patent application Ser. No. 16/122,857, filed on Sep. 5, 2018, which claims the benefit of the filing dates of provisional U.S. Patent Application No. 62/562,012, filed on Sep. 22, 2017, provisional U.S. Patent Application No. 62/562,078, filed on Sep. 22, 2017, and provisional U.S. Patent Application No. 62/562,110, filed on Sep. 22, 2017.

FIELD

The present disclosure generally relates to electrosurgical generators. More particularly, the present disclosure relates to systems and methods for providing, controlling, and applying electrosurgical energy for coagulation.

BACKGROUND

An electrosurgical generator is used in surgical procedures to provide electrical energy for treating the tissue of a patient. When bipolar forceps or another electrosurgical instrument is connected to the generator, the instrument can be used for cutting, coagulation, or sealing the tissue of a patient with high frequency electrical energy. During operation, electrical current from the generator flows between an active electrode and a return electrode of the instrument by passing through tissue and bodily fluids of a patient.

The electrical energy provided by the electrosurgical generator has different waveforms shaped to enhance its ability to cut, coagulate, or seal tissue. Different waveforms correspond to different modes of operating the generator, and each mode provides the surgeon various operating advantages. A surgeon can select and change various modes of operation as the surgical procedure progresses.

In the various modes, it is important to apply the appropriate amount of energy for the electrosurgical procedure. For example, applying too much energy may result in dissection or destruction of tissue. Applying too little energy may result in inhibiting the surgical procedure. Therefore, it is desirable to control the amount of energy provided by the electrosurgical generator for the surgical procedure being performed and for the operating conditions that are encountered. Accordingly, there is continued interest in developing and improving the control of electrical energy provided by an electrosurgical generator.

SUMMARY

The electrosurgical systems and methods of the present disclosure relate to systems and methods for providing, controlling, and applying electrosurgical energy for coagulation. As will be described in more detail, when a generator operates in coagulation mode to provide electrosurgical energy to an instrument, an adjustable voltage ramp rate is set based on a load impedance of a load of the instrument reaching a predetermined threshold, and voltage of the electrosurgical energy is changed based on the adjustable voltage ramp rate.

In one aspect of the disclosed technology, the disclosed technology includes an electrosurgical generator for providing electrical treatment energy to an instrument having an active electrode and a return electrode. The generator includes a processor and a memory storing instructions which are executable by the processor. When the instructions are executed, they cause the generator to control a treatment energy to the instrument in a coagulation mode, where the treatment energy has an adjustable voltage ramp rate which can be set to a ramp rate in a range of voltage ramp rates that effectuate coagulation and do not cause dissection of tissue in coagulation mode. The generator receives signals from the instrument over time relating to a load impedance between the active electrode and the return electrode of the instrument. When the load impedance is above a threshold, the generator sets the adjustable voltage ramp rate to a ramp rate in the range of voltage ramp rates, and decreases, at the adjustable voltage ramp rate, a voltage of the treatment energy being provided to the instrument. When the load impedance is below the threshold, the generator sets the adjustable voltage ramp rate to a ramp rate in the range of voltage ramp rates, and increases, at the adjustable voltage ramp rate, the voltage of the treatment energy being provided to the instrument.

In various embodiments, the threshold is between approximately five-hundred fifty ohms and five-hundred ohms. In various embodiments, when the load impedance is below the threshold, the adjustable voltage ramp rate is set to approximately one-hundred eighty volts per second, and when the load impedance is higher than the threshold, the adjustable voltage ramp rate is set to approximately two-hundred volts per second.

In various embodiments, the memory includes further instructions which, when executed by the processor, cause the generator to determine, based on the signals, that the instrument is currently grasping tissue and that, prior to the grasp, the instrument was not grasping tissue.

In various embodiments, in determining that the instrument is currently grasping tissue, the memory includes further instructions which, when executed by the processor, cause the generator to determine, based on the signals, that the instrument is currently grasping tissue and that, prior to the grasp, the instrument was not grasping tissue based on the load impedance decreasing from above a second threshold to below the second threshold. In various embodiments, the second threshold is approximately eight-thousand ohms.

In accordance with aspects of the present disclosure, the present disclosure includes a method for providing electrical treatment energy to an instrument having an active electrode and a return electrode, the method including controlling a treatment energy to provide to the instrument in a coagulation mode, where the treatment energy has an adjustable voltage ramp rate which can be set to a ramp rate in a range of voltage ramp rates that effectuate coagulation and do not cause dissection of tissue in the coagulation mode. The method includes receiving signals from the instrument over time relating to a load impedance between the active electrode and the return electrode of the instrument. When the load impedance is above a threshold, the method sets the adjustable voltage ramp rate to a ramp rate in the range of voltage ramp rates, and decreases, at the adjustable voltage ramp rate, a voltage of the treatment energy being provided to the instrument. When the load impedance is below the threshold, the method sets the adjustable voltage ramp rate to a ramp rate in the range of voltage ramp rates, and increases, at the adjustable voltage ramp rate, the voltage of the treatment energy being provided to the instrument.

In various embodiments, the threshold is between approximately five-hundred fifty ohms and five-hundred ohms. In various embodiments, when the load impedance is below the threshold, the adjustable voltage ramp rate is set to approximately one-hundred eighty volts per second, and when the load impedance is higher than the threshold, the adjustable voltage ramp rate is set to approximately two-hundred volts per second.

In various embodiments, the method determines, based on the signals, that the instrument is currently grasping tissue and that, prior to the grasp, the instrument was not grasping tissue. In various embodiments, the method determines that the instrument is currently grasping tissue and that, prior to the grasp, the instrument was not grasping tissue based on the load impedance decreasing from above a second threshold to below the second threshold. In various embodiments, the second threshold is approximately eight-thousand ohms.

In accordance with an aspect of the present disclosure, the present disclosure includes an electrosurgical system for providing electrical treatment energy. The system includes an instrument having an active electrode and a return electrode, and an electrosurgical generator configured to provide a treatment energy to the instrument. The generator includes a processor and a memory having instructions stored thereon. When the instructions are executed by the processor, they cause the generator to control a treatment energy to provide to the instrument in a coagulation mode, where the treatment energy has an adjustable voltage ramp rate which can be set to a ramp rate in a range of voltage ramp rates that effectuate coagulation and do not cause dissection of tissue in the coagulation mode. The generator receives signals from the instrument over time relating to a load impedance between the active electrode and the return electrode of the instrument. When the load impedance is above a threshold, the generator sets the adjustable voltage ramp rate to a ramp rate in the range of voltage ramp rates, and decreases, at the adjustable voltage ramp rate, the voltage of the treatment energy being provided to the instrument. When the load impedance is below the threshold, the generator sets the adjustable voltage ramp rate to a ramp rate in the range of voltage ramp rates, and increases, at the adjustable voltage ramp rate, the voltage of the treatment energy being provided to the instrument.

BRIEF DESCRIPTION OF THE DRAWINGS

Various embodiments of the present disclosure are described with reference to the accompanying drawings wherein:

FIG. 4 shows a flow chart of an exemplary operation of an electrosurgical system in accordance with aspects of the present disclosure.

DETAILED DESCRIPTION

The present disclosure relates to systems and methods for providing, controlling, and applying electrosurgical energy for coagulation. As will be described herein in more detail, in one aspect of the present disclosure, when a generator operates in coagulation mode to provide electrosurgical energy to an instrument, an adjustable voltage ramp rate is set based on a load impedance of a load of the instrument reaching a predetermined threshold, and voltage of the electrosurgical energy is changed based on the adjustable voltage ramp rate.

Where the term "approximately" is used herein in connection with a parameter having approximately a value, it is intended that the parameter can have exactly the value or can have another value which differs from the value due to environmental factors such as noise or due to hardware or software limitations such as, without limitation, number of bits or processor speed or interrupt priority.

Figure 1:
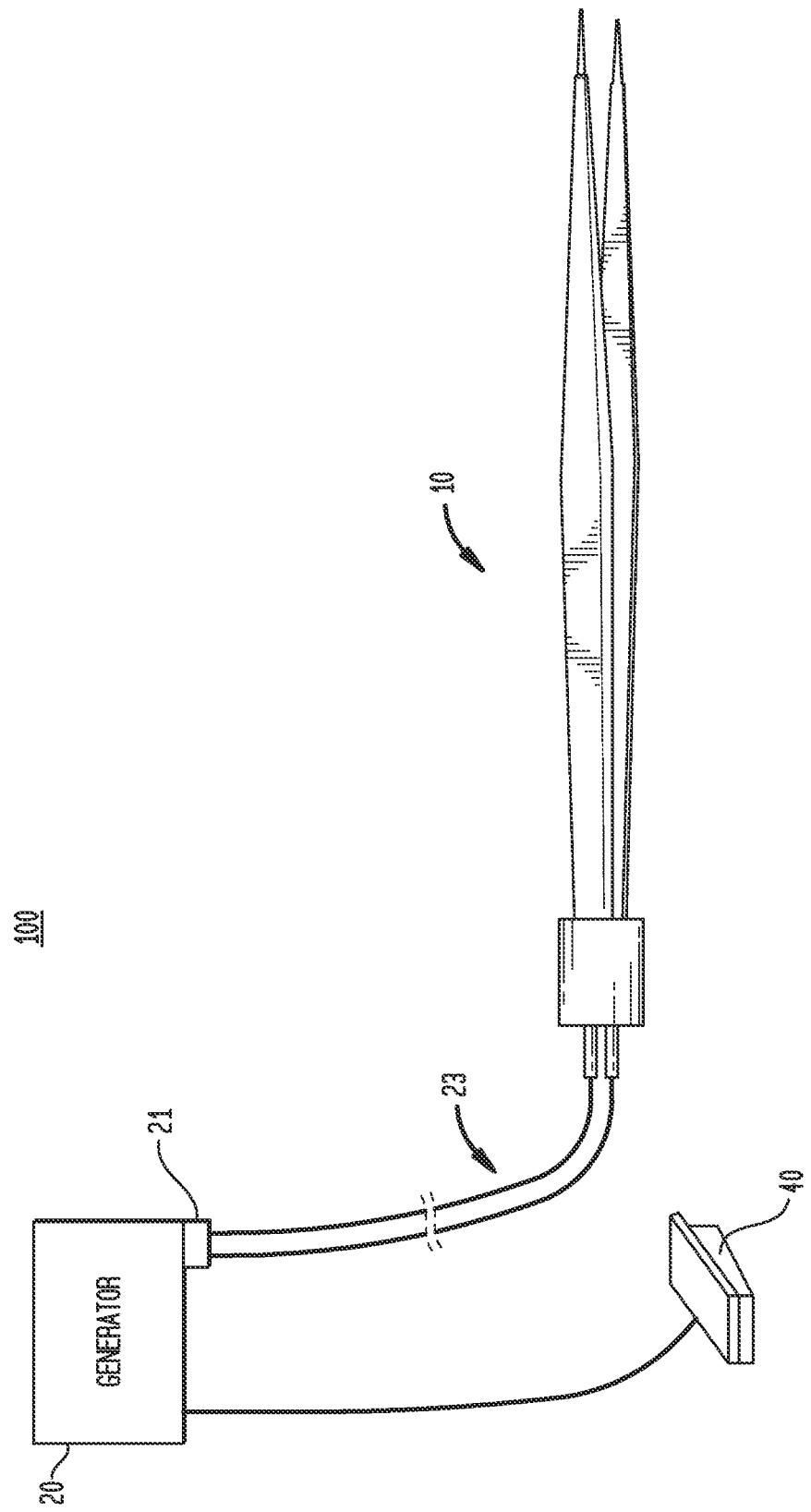
FIG. 1 is a schematic illustration, which shows an exemplary electrosurgical system including an electrosurgical generator in accordance with aspects of the present disclosure.

Referring now to FIG. 1, there is shown an illustration of an exemplary electrosurgical system 100 in accordance with aspects of the present disclosure. The system 100 includes an electrosurgical generator 20, an electrosurgical instrument 10, a cable 23 connecting the generator 20 and the instrument 10, and a foot switch 40. In various embodiments, the cable 23 and the instrument 10 may be separable. In various embodiments, the cable 23 may be attached to the instrument 10 and may be inseparable from the instrument 10. The generator 20 includes a port 21 that receives the cable 23. In various embodiments, the instrument 10 is a bipolar instrument and the port 21 of the generator 20 is a bipolar instrument port. As persons skilled in the art will recognize, a bipolar instrument receives electrical energy from a generator, applies a portion thereof to treat tissue, and returns a portion of the energy back to the generator. The instrument 10 illustrated in FIG. 1 is an exemplary bipolar forceps, which will be described in more detail in connection with FIG. 3. In various embodiments, the instrument 10 can be another type of bipolar electrosurgical instrument.

With continuing reference to FIG. 1, the generator 20 includes a user interface (not shown) that enables a user to set the generator 20 to provide electrical energy for different types of procedures. In various embodiments, the generator 20 can provide electrical energy for vessel coagulation, tissue dissection, or other types of electrosurgical procedures. Persons skilled in the art will understand the electrosurgical parameters generally suitable for such procedures. In various embodiments, the user interface (not shown) can include an energy setting that permits a user to specify an electrical energy for the generator 20 to provide to the instrument 10.

In FIG. 1, the system 100 also includes a foot switch 40 that is in communication with the generator 20. The foot switch 40 can be depressed to indicate to the generator 20 that electrical energy should be activated and provided to the instrument 10, and release of the foot switch 40 can indicate to the generator 20 that electrical energy should be deactivated. The illustrated embodiment of FIG. 1 is exemplary, and configurations, components, and devices other than those illustrated are contemplated to be within the scope of the present disclosure.

Figure 2:
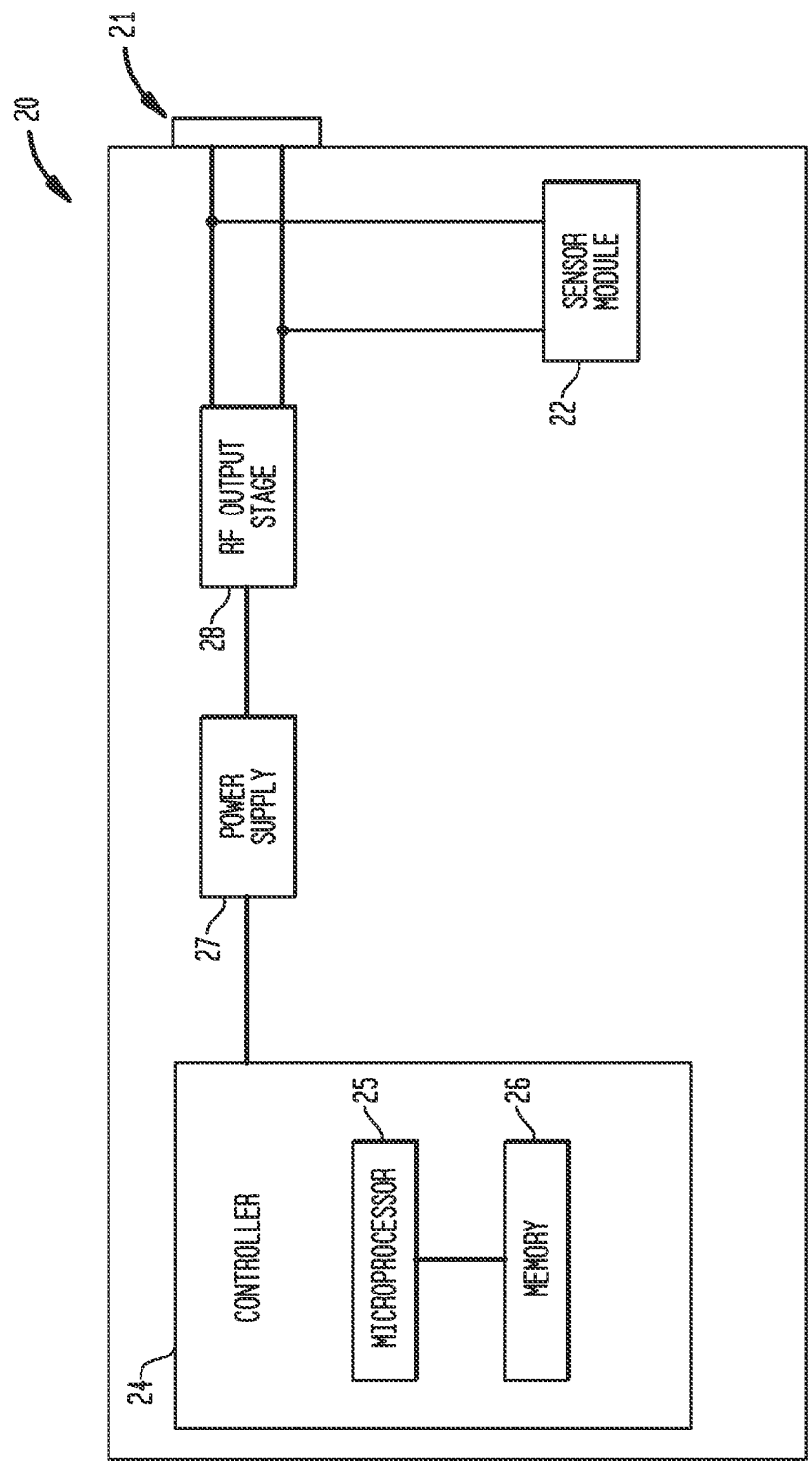
FIG. 2 shows a block diagram of exemplary components of the electrosurgical generator of FIG. 1 in accordance with aspects of the present disclosure.

Referring now to FIG. 2, there is shown a block diagram of exemplary components of an electrosurgical generator 20 in accordance with aspects of the present disclosure. In the illustrated embodiment, the generator 20 includes a controller 24, a power supply 27, a radio-frequency (RF) energy output stage 28, a sensor module 22, and one or more connector ports 21 that accommodate various types of electrosurgical instruments. The generator 20 can include a user interface (not shown), which permits a user to select various parameters for the generator 20, such as mode of operation and power setting. The mode of operation can include, for example, coagulation mode and tissue dissection mode. In various embodiments, the power setting can be specified by a user to be between zero and a power limit, such as, for example, five watts, thirty watts, seventy watts, or ninety-five watts.

In the illustrated embodiment, the controller 24 includes a microprocessor 25 and a memory 26. In various embodiments, the controller 24 or the microprocessor 25 may be another type of processor such as, without limitation, a digital signal processor, a field-programmable gate array (FPGA), or a central processing unit (CPU). In various embodiments, the memory 26 can be random access memory, read only memory, magnetic disk memory, solid state memory, optical disc memory, and/or another type of memory. In various embodiments, the memory 26 can be separate from the controller 24 and can communicate with the microprocessor 25 through communication buses of a circuit board and/or through communication cables such as serial ATA cables or other types of cables. The memory 26 includes machine instructions that are executable by the microprocessor 25 to operate the generator 20. Various operations of the generator 20 are described below. Such operations can be controlled by the machine instructions executed by the microprocessor 25.

With continuing reference to FIG. 2, in various embodiments, the power supply 27 can be a converter that receives AC energy, such as AC energy from a wall outlet, and converts the AC energy to DC energy. The power supply 27 can provide power to the controller 24 and can also be controllable by the controller 24. For example, the controller 24 can control the power supply 27 based on a user-specified energy setting. The DC energy produced by the power supply 27 is conveyed to the RF energy output stage 28. In various embodiments, the RF output stage 28 coverts the DC energy into an AC electrical waveform and conveys the waveform to an electrosurgical instrument through the connector port 21. In various embodiments, the RF output stage 28 can include an H-bridge that drives a resonant tank. Persons skilled in the art will understand the various implementations of the power supply 27 and the RF output stage 28, and will understand the AC electrical waveforms suitable for coagulation, tissue dissection, and other operations.

With continuing reference to FIG. 2, the sensor module 22 can include a voltage sensor and a current sensor, among other types of sensors. In various embodiments, the sensor module 22 and the controller 24 can cooperate to determine or estimate a load impedance of a load of the instrument. For example, the controller 24 can direct the RF output stage 28 to generate a non-therapeutic electrical waveform that can be used to determine or estimate a load impedance of a load of the instrument. The non-therapeutic electrical waveform corresponds to a voltage and current provided from the generator 20 to the instrument through the connector port 21 and corresponds to a return current that returns from the instrument to the generator 20 through the connector port 21. The return current can be sensed by the sensor module 22, which can communicate the return current measurements to the controller 24. The controller 24 can use the return current measurements to determine or estimate the load impedance of a load of the instrument. For example, the load impedance can be determined or estimated as the voltage provided by the RF output stage 28 divided by the sensed return current. In various embodiments, the voltage sensor of the sensor module 22 can sense the voltage provided to the connector port 21, and the sensed voltage can be used with the sensed return current to determine or estimate the load impedance of a load of the instrument. For example, the load impedance can be determined or estimated as the sensed voltage divided by the sensed return current. As will be described in more detail in connection with FIG. 4, if the load impedance is greater than a predetermined threshold, such as approximately eight-thousand ohms, the controller 24 can determine that the instrument is not grasping tissue. On the other hand, if the load impedance is less than a predetermined threshold, such as four ohms, the controller 24 can determine that the active and return electrodes of the instrument are shorted together. Otherwise, the controller 24 can determine that the instrument is grasping tissue.

In various embodiments, the controller 24 and the sensor module 22 can determine whether the instrument is grasping tissue in other ways. As mentioned above, a user can set an energy setting at the generator 20, and the generator 20 can control the voltage and/or current provided by the power supply 27 and RF output stage 28 to provide the indicated energy. When the instrument is not grasping tissue, no meaningful current is drawn by the instrument. Thus, no treatment energy is actually provided by the generator 20 to the instrument, and the voltage at the output of the RF output stage 28 stays essentially the same. When the instrument grasps tissue, a current is then drawn by the instrument, which causes the generator 20 to vary the voltage to provide the indicated treatment energy setting. The variations in voltage can be characterized using a parameter known as crest factor, which persons skilled in the art will understand as a ratio of peak voltage to root-mean-squared (RMS) voltage. In various embodiments, the sensor module 22 can include one or more voltage sensors that measure voltages and can communicate the measurements to the controller 24 for the purpose of determining crest factor. In various embodiments, if the crest factor is greater than a predetermined threshold, the controller can determine that the instrument has grasped tissue. The illustrated embodiment of FIG. 2 is exemplary, and configurations, components, and devices other than those illustrated are contemplated to be within the scope of the present disclosure.

Figure 3:
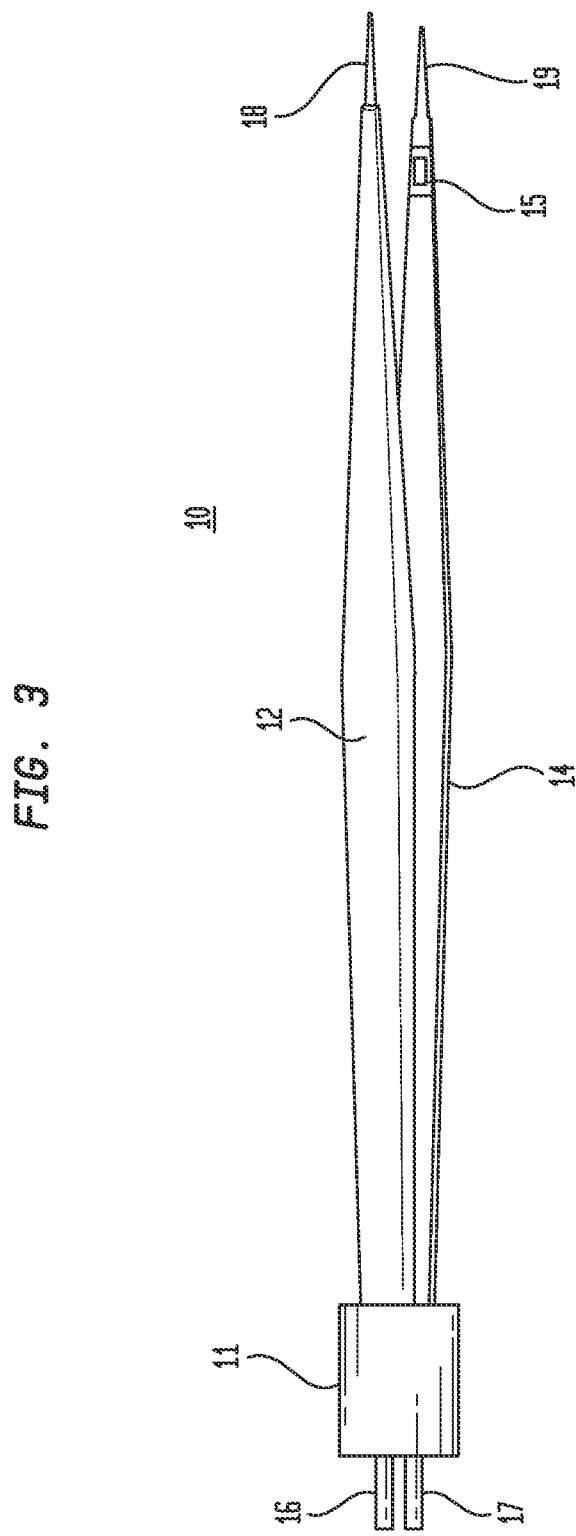
FIG. 3 shows a diagram of the electrosurgical instrument of FIG. 1.

FIG. 3 is an illustration of an exemplary instrument in accordance with aspects of the present disclosure. The instrument illustrated in FIG. 3 is a bipolar forceps 10, which may be used for various procedures such as vessel coagulation and tissue dissection. The bipolar forceps 10 includes an electrical connector 11 with two terminals 16, 17 configured to connect to an electrosurgical generator through a cable. One terminal 16 can convey current from the generator to the instrument 10, and the other terminal 17 can return current from the instrument 10 back to the generator.

The electrical connector 11 is attached to two arms 12, 14 that extend from the electrical connector 11. The two arms 12, 14 terminate in electrodes 18, 19 at the end opposite the electrical connector 11. One electrode 18 is referred to herein as an active electrode, and the other electrode 19 is referred to as a return electrode. The active electrode 18 conveys current received from the generator, and the return electrode 19 returns current back to the generator. The two arms 12, 14 include conductors (not shown) that connect the terminals 16, 17 of the electrical connector 11 with the electrodes 18, 19. Additionally, the two arms 12, 14 are mechanically biased away from each other so that the arms 12, 14 are apart in their resting state. A surgeon using the bipolar forceps 10 can squeeze the arms 12, 14 with varying amounts of force to press the arms 12, 14 and the electrodes 18, 19 closer together and to grasp tissue between the electrodes 18, 19.

In accordance with one aspect of the present disclosure, the instrument 10 can include one or more sensors 15 for determining whether the instrument 10 is grasping tissue. In connection with FIG. 3, the sensor 15 can be located on one or both of the arms 12, 14. In various embodiments, the sensor 15 can be a pressure sensor that indicates whether tissue is in contact with the pressure sensor. In various embodiments, the sensor 15 can be a light sensor that indicates whether tissue is occluding light from reaching the light sensor. The pressure sensor and/or the light sensor can be located in proximity to the active and return electrodes 18, 19, such that the sensor signals are indicative or whether the active and return electrodes 18, 19 are grasping tissue. In various embodiments, the sensor 15 can be arranged at another location of the instrument 10 as long as the sensor signals would be indicative of whether the active and return electrodes 18, 19 are grasping tissue. In various embodiments, the instrument 10 can include a manual switch (not shown) which a user can toggle to manually indicate whether tissue is grasped by the instrument 10. The signals from the pressure sensor, the light sensor, or the manual switch can be communicated from the instrument 10 to the generator. In various embodiments, the signals can be communicated using the terminals 16, 17 of the electrical connector 11. In various embodiments, the signals can be communicated using another conductor in the cable (FIG. 1, 23) connecting the instrument 10 and the generator, and the electrical connector 11 can include a third terminal (not shown) for this communication.

The illustrated embodiment of FIG. 3 is exemplary, and other instruments are contemplated to be within the scope of the present disclosure. In various embodiments, the instrument 10 can be another electrosurgical instrument that permits a surgeon to exert varying degrees of pressure on tissue by applying varying degrees of force to the instrument, such as Kleppinger forceps.

What have been described above are systems, methods, and devices for producing, controlling, and applying electrosurgical energy. The following will describe methods for controlling electrosurgical energy during a coagulation procedure.

As mentioned above, a user can set an electrical treatment power for the generator using a user interface. Because power is the product of voltage and current, the generator will generally attempt to provide the indicated electrical power by adjusting current and/or voltage. That is, if the indicated power is denoted as $Ps = V \cdot I$, the generator attempts to vary V and/or I so that their product results in Ps.

Additionally, the current actually flowing through the instrument depends on the load impedance of the tissue being treated by the instrument. Tissue impedance can change for various reasons. In various situations, tissue impedance can increase when tissue temperature increases. Also, as tissue becomes desiccated, the tissue's moisture content drops, causing the tissue's impedance to rise. Additionally, in the case of forceps where a surgeon can exert varying degrees of pressure on tissue by applying varying degrees of force to the instrument, tissue impedance can increase with increasing pressure applied to the tissue. If the load impedance is denoted as ZL, then the current is $I = V/ZL$. Combining the power and impedance equations, it can be seen that $Ps = V2/ZL$. Based on this relationship, when the load impedance ZL increase, the generator attempts to maintain the indicated electrical power Ps by increasing the voltage V so that $V2/ZL = Ps$ is maintained. Thus, when load impedance increases, the generator increases voltage in order to maintain a particular power setting.

When using electrosurgical energy for coagulation, it has been found that applying too much voltage to the tissue can cause unintended dissection, even when the generator operates in coagulation mode. Because generator voltage increases with tissue impedance, as discussed above, the voltage may reach a certain point where dissection occurs. In accordance with one aspect of the present disclosure, the generator can decrease voltage to prevent the voltage from rising so high that it causes dissection in the coagulation mode. Based on $Ps = V2/ZL$, decreasing voltage will also decrease the power provided by the generator. At a certain point, providing too little power will result in insufficient coagulation. Therefore, to sustain sufficient coagulation, the generator will need to increase the voltage and power at a certain point.

In accordance with one aspect of the present disclosure, it has been found that decreasing the power provided by the generator causes the tissue impedance to decrease. Because increased tissue impedance corresponds with increasing generator voltage, and decreasing generator voltage and power corresponds with decreased tissue impedance, tissue impedance can, in accordance with an aspect of the present disclosure, be used to control voltage and power in the coagulation mode to maintain coagulation and mitigate unintentional dissection. As discussed in connection with FIG. 2, the sensor module 22 and the controller 24 can be used to determine load impedance of a load of the instrument. Thus, the controller 24 can determine load impedance and use the load impedance to control generator power and voltage.

As will be explained in more detail in connection with FIG. 4, when the load impedance is greater than a certain threshold, the generator decreases voltage at a particular ramp rate, and when the load impedance is lower than the threshold, the generator increases the voltage a particular ramp rate. In various embodiments, the threshold can be between approximately five-hundred to approximately five-hundred fifty ohms, inclusive. For example, the threshold can be approximately five-hundred ohms or can be approximately five-hundred fifty ohms. These parameters can be stored in the memory. (FIG. 2, 26.)

Additionally, the voltage ramp rates are appropriately selected. If voltage ramp rates are too high, the voltage would return to a high voltage too quickly and expose the tissue to high voltages, possibly causing tissue dissection in the coagulation mode. And if voltage ramp rates are too low, the operating time of the procedure may extend too long. In various embodiments, voltage ramp rates can be between approximately sixty volts per second and approximately four-hundred thirty volts per second. In various embodiments, when the load impedance is greater than the threshold, the voltage may be reduced at, for example, a ramp rate of approximately two-hundred volts per second. In various embodiments, when the load impedance is below the threshold, the voltage may be increased at, for example, a ramp rate of approximately one-hundred eighty volts per second. These parameters can be stored in the memory. (FIG. 2, 26.)

Referring now to FIG. 4, there is shown a flow chart of a generator operation for providing treatment power to an instrument having an active electrode and a return electrode. At step 402, the generator operates in coagulation mode and controls a treatment energy to provide to the instrument in the coagulation mode. The treatment energy has an adjustable voltage ramp rate that can be set to a ramp rate in a range of voltage ramp rates that effectuate coagulation but do not cause dissection of tissue in the coagulation mode. In various embodiments, the adjustable voltage ramp rate can be set to a voltage ramp rate that causes voltage to quickly reach high voltages that may cause dissection of tissue in the coagulation mode. Such a ramp rate may be used, for example, only at the initiation of treatment energy. After initiation, the voltage ramp rate may be changed to a ramp rate that effectuates coagulation but does not cause dissection of tissue in the coagulation mode.

At step 404, the generator receives signals from the instrument over time relating to a load impedance between the active and return electrodes of the instrument. As discussed in connection with FIG. 2, the signals can be return current returned from the instrument 10 to the generator 20 based on a non-therapeutic electrical waveform.

At step 406, the generator determines, based on the signals, that the instrument is currently grasping tissue and that, prior to the grasp, the instrument was not grasping tissue. As described in connection with FIG. 2, load impedance can be used to determine whether or not the instrument 10 is grasping tissue. If the load impedance is less than a predetermined threshold, such as approximately four ohms, the controller 24 can determine that the active and return electrodes of the instrument are shorted together. If the load impedance is greater than the predetermined threshold and is lower than another predetermined threshold, such as approximately eight-thousand (8000) ohms, the controller 24 can determine that the instrument is grasping tissue. Prior to the tissue grasp, the load impedance determined by the controller 24 can indicate that the active electrode 18 and the return electrode 19 were not grasping tissue based on the load impedance being greater than approximately eight-thousand (8000) ohms.

In response to the determination that the instrument is currently grasping tissue and that, prior to the grasp, the instrument was not grasping tissue, the generator, at step 408, sets the adjustable voltage ramp rate to an initial voltage ramp rate. In various embodiments, the voltage of the treatment energy is changed at the initial voltage ramp rate until the load impedance reaches the impedance threshold. As discussed above, the threshold can be between approximately five-hundred and five-hundred fifty ohms, inclusive. For example, the load impedance threshold can be approximately five-hundred ohms, or the load impedance threshold can be approximately five-hundred fifty ohms. In various embodiments, the initial voltage ramp rate can be a ramp rate that causes the voltage to quickly reach high voltages that may cause dissection in the coagulation mode, and can be approximately nine-hundred volts per second.

At step 410, when the load impedance is above the threshold, the generator sets the adjustable voltage ramp rate to a ramp rate in the range of voltage ramp rates that effectuate coagulation without causing tissue dissection, and decreases, at the adjustable voltage ramp rate, the voltage of the treatment energy being provided to the instrument. As mentioned above, the range of voltage ramp rates that effectuate coagulation without causing tissue dissection can be between approximately sixty volts per second and approximately four-hundred thirty volts per second. For example, when the load impedance is greater than the threshold, the voltage may be reduced at a ramp rate of approximately two-hundred volts per second.

At step 412, when the load impedance is below the threshold, the generator sets the adjustable voltage ramp rate to a ramp rate in the range of voltage ramp rates that effectuate coagulation without causing tissue dissection, and increases, at the adjustable voltage ramp rate, the voltage of the treatment energy being provided to the instrument. For example, when the load impedance is below the threshold, the voltage may be increased at a ramp rate of approximately one-hundred eighty volts per second.

At step 414, the generator determines whether the instrument is still grasping tissue. If the instrument is still grasping tissue, the illustrated operation returns to step 410. Otherwise, the illustrated operation ends.

Referring also to FIG. 2, the memory 26 can store various parameters for controlling the electrosurgical energy, such as power limit, voltage limit, current limit, ramp rate of power changes, ramp rate of voltage changes, and ramp rate of current changes, among other parameters. In various embodiments, these parameters are adjustable. In various embodiments, the power limit, the voltage limit, and the current limit are less than the maximum power, voltage, and current, respectively, that the generator 20 is capable of providing to the instrument.

In various embodiments, when the controller 24 controls the treatment energy to increase the voltage of the treatment energy, the voltage is increased up to the voltage limit. In various embodiments, the sensor module 22 can sense the voltage provided by the RF output stage. When the sensed voltage reaches the voltage limit, the controller 24 can stop increasing the voltage of the treatment energy. In various embodiments, if the sensed voltage exceeds the voltage limit, the controller 24 can decrease the voltage of the treatment energy so that it decreases to the voltage limit or to below the voltage limit. In various embodiments, changes to the current of the treatment energy are subject to the current limit and the current ramp rate. In various embodiments, changes to treatment energy are subject to the power limit and the power ramp rate.

Accordingly, what have been described are systems, methods, and devices for providing, controlling, and applying electrosurgical energy. Although the illustrative embodiments of the present disclosure have been described herein with reference to the accompanying drawings, it is to be understood that the disclosure is not limited to those precise embodiments, and that various other changes and modification may be effected therein by one skilled in the art without departing from the scope or spirit of the disclosure.

What is claimed is:

1. An electrosurgical generator, comprising:
 a processor; and
 a memory having stored thereon instructions which, when executed by the processor, cause the electrosurgical generator to:
  control delivery of a treatment energy to an instrument, the treatment energy having an adjustable voltage ramp rate, wherein the adjustable voltage ramp rate is configured to be set to a ramp rate in a range of voltage ramp rates that effectuate coagulation before dissection and prevent dissection of grasped tissue;
  receive signals from the instrument over time relating to a load impedance between a first electrode and a second electrode of the instrument;
  when the load impedance is above a first threshold of a plurality of thresholds, select a voltage ramp rate from a plurality of voltage ramp rates in the range of voltage ramp rates to set the adjustable voltage ramp rate to the selected voltage ramp rate, and decrease, at the adjustable voltage ramp rate, a voltage of the treatment energy being delivered to the instrument, wherein each voltage ramp rate of the plurality of voltage ramp rates is associated with at least one threshold of the plurality of thresholds; and
  when the load impedance is below the first threshold, set the adjustable voltage ramp rate to a ramp rate in the range of voltage ramp rates, and increase, at the adjustable voltage ramp rate, the voltage of the treatment energy being delivered to the instrument.

2. The electrosurgical generator of claim 1, wherein the first threshold is about 500 ohms to about 550 ohms.

3. The electrosurgical generator of claim 1, wherein when the load impedance is below the first threshold, the adjustable voltage ramp rate is set to approximately 180 volts per second, and when the load impedance is higher than the first threshold, the adjustable voltage ramp rate is set to approximately 200 volts per second.

4. The electrosurgical generator of claim 1, wherein the adjustable voltage ramp rate is configured to be set to another voltage ramp rate that causes a dissection of tissue, and the other voltage ramp rate is greater than the range of voltage ramp rates.

5. The electrosurgical generator of claim 1, wherein the memory includes further instructions which, when executed by the processor, cause the electrosurgical generator to determine that the instrument is currently grasping tissue.

6. The electrosurgical generator of claim 5, wherein in determining that the instrument is currently grasping tissue, the memory includes further instructions which, when executed by the processor, cause the electrosurgical generator to determine, based on the signals, that prior to grasping the tissue, the instrument was not grasping the tissue based on the load impedance decreasing from above a second threshold to below the second threshold.

7. The electrosurgical generator of claim 6, wherein the second threshold is approximately 8,000 ohms.

8. A method for providing electrical treatment energy to an instrument, the method comprising:
controlling delivery of a treatment energy to an instrument, the treatment energy having an adjustable voltage ramp rate, wherein the adjustable voltage ramp rate can be set to a ramp rate in a range of voltage ramp rates that effectuate coagulation before dissection and prevent dissection of grasped tissue;
receiving signals from the instrument over time relating to a load impedance between an active electrode of the instrument and a return electrode of the instrument;
when the load impedance is above a first threshold of a plurality of thresholds, selecting a voltage ramp rate from a plurality of voltage ramp rates in the range of voltage ramp rates to set the adjustable voltage ramp rate to the selected voltage ramp rate, and decreasing, at the adjustable voltage ramp rate, a voltage of the treatment energy being delivered to the instrument, wherein each voltage ramp rate of the plurality of voltage ramp rates is associated with at least one threshold of the plurality of thresholds; and
when the load impedance is below the first threshold, setting the adjustable voltage ramp rate to a ramp rate in the range of voltage ramp rates, and increasing, at the adjustable voltage ramp rate, the voltage of the treatment energy being delivered to the instrument.

9. The method of claim 8, wherein the first threshold is about 500 ohms to about 550 ohms.

10. The method of claim 8, wherein when the load impedance is below the first threshold, the adjustable voltage ramp rate is set to approximately 180 volts per second, and when the load impedance is higher than the first threshold, the adjustable voltage ramp rate is set to approximately 200 volts per second.

11. The method of claim 8, wherein the adjustable voltage ramp rate is configured to be set to another voltage ramp rate that causes a dissection of tissue, wherein the other voltage ramp rate is greater than the range of voltage ramp rates.

12. The method of claim 8, further comprising:
determining that the instrument is currently grasping tissue; and
determining, based on the signals, that prior to grasping the tissue, the instrument was not grasping the tissue.

13. The method of claim 12, wherein the determining that the instrument is currently grasping tissue and that, prior to grasping the tissue, the instrument was not grasping the tissue is based on the load impedance decreasing from above a second threshold to below the second threshold.

14. The method of claim 13, wherein the second threshold is approximately 8,000 ohms.

15. An electrosurgical system, comprising:
an instrument having an active electrode and a return electrode; and
an electrosurgical generator configured to provide a treatment energy to the instrument, the electrosurgical generator including:
a processor; and
a memory having stored thereon instructions which, when executed by the processor, cause the electrosurgical generator to:
control delivery of a treatment energy to the instrument, the treatment energy having an adjustable voltage ramp rate, wherein the adjustable voltage ramp rate is configured to be set to a ramp rate in a range of voltage ramp rates that effectuate coagulation before dissection and prevent dissection of grasped tissue;
receive signals from the instrument over time relating to a load impedance between the active electrode and the return electrode of the instrument;
when the load impedance is above a first threshold of a plurality of thresholds, select a voltage ramp rate from a plurality of voltage ramp rates in the range of voltage ramp rates to set the adjustable voltage ramp rate to the selected voltage ramp rate, and decrease, at the adjustable voltage ramp rate, a voltage of the treatment energy being delivered to the instrument, wherein each voltage ramp rate of the plurality of voltage ramp rates are associated with at least one threshold of the plurality of thresholds; and
when the load impedance is below the first threshold, set the adjustable voltage ramp rate to a ramp rate in the range of voltage ramp rates, and increase, at the adjustable voltage ramp rate, the voltage of the treatment energy being delivered to the instrument.

16. The electrosurgical system of claim 15, wherein the first threshold is about 500 ohms to about 550 ohms.

17. The electrosurgical system of claim 15, wherein when the load impedance is below the first threshold, the adjustable voltage ramp rate is set to approximately 180 volts per second, and when the load impedance is higher than the first threshold, the adjustable voltage ramp rate is set to approximately 200 volts per second.

18. The electrosurgical system of claim 16, wherein the adjustable voltage ramp rate is configured to be set to another voltage ramp rate that causes a dissection of tissue, and the other voltage ramp rate is greater than the range of voltage ramp rates.

19. The electrosurgical system of claim 16, wherein the memory includes further instructions which, when executed by the processor, cause the electrosurgical generator to determine the instrument is currently grasping tissue.

20. The electrosurgical system of claim 19, wherein in determining that the instrument is currently grasping tissue, the memory includes further instructions which, when executed by the processor, cause the electrosurgical generator to determine, based on the signals, that prior to grasping the tissue, the instrument was not grasping the tissue based on the load impedance decreasing from above a second threshold to below the second threshold.

* * * * *